United States Patent [19]
Kiel

[11] Patent Number: 6,015,927
[45] Date of Patent: *Jan. 18, 2000

[54] PROCESS FOR PREPARING CYCLOHEXANONES BY HYDROGENATION OF THE CORRESPONDING PHENOLS (II)

[75] Inventor: Wolfgang Kiel, Odenthal, Germany

[73] Assignee: Bayer Aktiengesellschaft, Leverkusen, Germany

[ * ] Notice: This patent is subject to a terminal disclaimer.

[21] Appl. No.: 09/106,815

[22] Filed: Jun. 29, 1998

[30] Foreign Application Priority Data

Jun. 30, 1997 [DE] Germany .......................... 197 27 710

[51] Int. Cl.$^7$ .................................... C07C 45/29
[52] U.S. Cl. .................... 568/362; 568/376; 568/799; 568/814
[58] Field of Search .................... 568/308, 309, 568/325, 326, 327, 329, 330, 338, 362, 376, 379, 403, 799, 814

[56] References Cited

U.S. PATENT DOCUMENTS

| | | | |
|---|---|---|---|
| 2,829,166 | 4/1958 | Joris et al. | 260/586 |
| 3,076,810 | 2/1963 | Duggan et al. | 260/586 |
| 3,998,884 | 12/1976 | Gibson | 260/586 P |
| 4,200,553 | 4/1980 | Van Peppen et al. | 252/447 |
| 4,304,943 | 12/1981 | Bjornson | 568/361 |

FOREIGN PATENT DOCUMENTS

| | | |
|---|---|---|
| 0731075 A1 | 9/1996 | European Pat. Off. . |
| 2909780 | 9/1980 | Germany . |
| 1512497 | 6/1978 | United Kingdom . |
| 1563044 | 3/1980 | United Kingdom . |

OTHER PUBLICATIONS

Nishimura et al, Bull.Chem.Soc.Jpn., 65, 2955–2959, 1992.

*Primary Examiner*—Gary Geist
*Assistant Examiner*—Sreeni Padmanabhan
*Attorney, Agent, or Firm*—Brinks Hofer Gilson & Lione

[57] ABSTRACT

Substituted or unsubstituted cyclohexanones are advantageously prepared by hydrogenation of the corresponding phenols in the presence of a palladium-on-carbon catalyst at from 100 to 250° C. and from 1 to 20 bar of hydrogen pressure if the reaction is carried out in the presence of straight-chain, branched or cyclic alkanes having a boiling point at atmospheric pressure of over 70° C. as solvents. This makes it possible to obtain substituted or unsubstituted cyclohexanones in short hydrogenation times and in high yields using low-toxicity, physically problem-free solvents which are easy to handle from a safety point of view.

18 Claims, No Drawings

PROCESS FOR PREPARING CYCLOHEXANONES BY HYDROGENATION OF THE CORRESPONDING PHENOLS (II)

BACKGROUND OF THE INVENTION

The present invention relates to an advantageous process for the hydrogenation of phenols to give the corresponding cyclohexanones using palladium-on-carbon catalysts.

Processes for the hydrogenation of phenols over palladium-on-carbon catalysts to give cyclohexanones are known in principle (see, for example, DE-A 2 909 780, DE-A 2 530 759 (G.B. 1,512,497) and U.S. Pat. No. 2,829, 166).

In general, to achieve a good selectivity, a hydrogen pressure of less than 20 bar and a reaction temperature in the range from 120 to 250° C. are sought and an alkaline compound is added to the hydrogenation mixture. The catalyst can, if desired, be treated with alkali metal ions such as Na or K ions (see, for example, German Auslegeschrift 1 144 267 (U.S. Pat. No. 3,076,810)). The use of phenoxides and bicarbonates is described in FR-A 2 372 136 (G.B. 1,563,044).

According to DE-A 2 909 780, sodium carbonate, borax and/or sodium acetate are used for the hydrogenation of p-tert-amylphenol. At the same time, it is indicated here that the use of palladium catalysts having metal surface areas of 15 m²/g and more is promising. Preference is given to using palladium-on-carbon catalysts containing 5% by weight of palladium, based on a support which has a surface area of 800 m²/g.

A disadvantage of these known processes is that only solvents which are difficult to handle from a technical and/or toxicological point of view are known for the reaction of phenols having high melting points (see, for example, EP-A 731 075). It would be desirable to have solvents which are nontoxic and safe to handle and can be separated off physically without problems and at little expense.

In addition, long reaction times are frequently required, particularly when phenols which are liquid at the hydrogenation temperature and no solvents are used.

SUMMARY OF THE INVENTION

The invention provides a method of making cyclohexanones by hydrogenation of the corresponding phenols.

DESCRIPTION OF THE INVENTION

A process has now been found for preparing cyclohexanones of the formula (I)

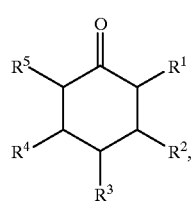

(I)

where
$R^1$, $R^2$, $R^3$, $R^4$ and $R^5$ are each, independently of one another, hydrogen, hydroxy, $C_1$–$C_{10}$-alkyl, $C_3$–$C_6$-cycloalkyl, $C_6$–$C_{10}$-aryl, $C_6$–$C_{10}$-aryl—$CH_2$—, $C_6$–$C_{10}$-aryl—O—, $C_1$–$C_{10}$-alkoxy, $C_3$–$C_8$-cycloalkoxy, $C_1$–$C_4$-alkylamino, di-$C_1$–$C_4$-alkylamino, $C_1$–$C_4$-acylamino, $COOR^6$ where $R^6$=hydrogen or $C_1$–$C_4$-alkyl or $R^7$—$CH_2$— where $R^7$=hydroxy, $C_1$–$C_4$-alkoxy, $C_1$–$C_4$-alkylamino or di-$C_1$–$C_4$-alkylamino, by hydrogenation of phenols of the formula (II)

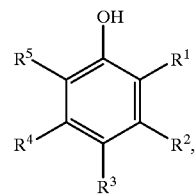

(II)

where $R^1$ to $R^5$ are as defined for formula (1), in the presence of a palladium-on-carbon catalyst at from 100 to 250° C. and from 1 to 20 bar of hydrogen pressure, wherein the reaction is carried out in the presence of straight-chain, branched or cyclic alkanes having a boiling point at atmospheric pressure of over 70° C. as solvents.

In the formulae (I) and (II), $R^1$, $R^2$, $R^3$, $R^4$ and $R^5$ preferably represent, independently of one another, hydrogen, hydroxy, $C_1$–$C_6$-alkyl, $C_1$–$C_6$-alkoxy or $C_1$–$C_4$-acylamino. It is also preferred that from 1 to 4 of the radicals $R^1$ to $R^5$ are different from hydrogen.

Examples of $C_1$–$C_6$-alkyl are methyl, ethyl, i-propyl, t-butyl and pentyl. Examples of $C_1$–$C_6$-alkoxy are methoxy, ethoxy and i-propoxy. An example of $C_1$–$C_4$-acylamino is acetylamino.

Particularly preferably, $R^1$, $R^2$, $R^4$ and $R^5$ represent hydrogen and $R^3$ represents hydroxy, $C_1$–$C_6$-alkyl, $C_1$–$C_6$-alkoxy or $C_1$–$C_4$-acylamino.

The palladium-on-carbon catalysts can comprise, for example, from 1 to 15% by weight of palladium on any carbon. These catalysts preferably contain from 2 to 12% by weight of palladium. Such catalysts are commercially available. They are frequently supplied in a form which is moist with water and can also be used in this form which is moist with water. Based on the phenol of the formula (II), it is possible to use, for example, from 0.001 to 1% by weight of catalyst (calculated as Pd metal). This amount is preferably from 0.05 to 0.2 % by weight.

The reaction temperature is preferably from 150 to 200° C. and the hydrogen pressure is preferably from 3 to 8 bar.

It is an essential feature of the present invention that straight-chain, branched or cyclic alkanes which have a boiling point at atmospheric pressure of over 70° C. are used as solvents. Suitable solvents are, for example, straight-chain and branched $C_7$–$C_{18}$-alkanes, unsubstituted $C_6$–$C_{10}$-cycloalkanes and $C_6$–$C_{10}$-cycloalkanes substituted by straight-chain or branched $C_{1-10}$-alkyl groups. Preferred solvents are isooctane, cyclohexane and methylcyclohexane. Particular preference is given to methylcyclohexane. It is also possible to use mixtures of various solvents.

Based on 100 g of the phenol of the formula (II) which is used, it is possible to use, for example, from 10 to 1000 ml of the solvents to be used according to the invention. This amount is preferably from 50 to 300 ml.

In a particular embodiment of the process of the invention, the catalyst is not used as such or in a form which is moist with water, but it is mixed beforehand with a base component and from 20 to 200% by weight of water (based on the base component). Suitable base components are, in particular, alkali metal salts which have a basic reaction in aqueous medium. Preference is given to borax ($Na_2B_4O_7 \times 10H_2O$), sodium acetate and disodium hydrogen phosphate. Based on the palladium-on-carbon catalyst, it is possible to use, for example, from 5 to 50% by weight of base component. This amount is preferably from 10 to 20% by weight.

Based on the base component, the amount of water is preferably from 50 to 150% by weight. The amount of water to be used does not include any water of crystallization present in the base component. Likewise, any water which has been used for moistening the catalyst to improve its handling is not taken into account. It is advantageous first to mix the base component with water, with it being of no consequence whether the base component dissolves completely or not, and then to mix the base component/water mixture with the dry or moist palladium-on-carbon catalyst.

In principle, phenols of the formula (II) which have a melting point below the desired hydrogenation temperature can be hydrogenated in the melt without addition of solvent. However, it has been found that even in these cases the addition of solvents to be employed according to the invention is advantageous because this greatly increases the hydrogenation rate.

The process of the invention can be carried out, for example, in stirred or loop reactors.

The process of the invention has the advantages that it enables cyclohexanones of the formula (I) to be prepared in short hydrogenation times and in high yields using low-toxicity, physically problem-free solvents which are easily handled from a safety point of view and can readily be separated off. After the reaction, the solvent frequently forms a separate, virtually catalyst- and product-free phase which can be separated off simply and reused in the next batch. This can be done, for example, in the hydrogenation of hydroquinone to p-hydroxycyclohexanone in the presence of methylcyclohexane as solvent.

EXAMPLES

Example 1

0.5g of borax and 0.5 g of water were mixed and 6 g of a catalyst which was moist with water (water content=50 %) and comprised 5% by weight of palladium on carbon were then mixed in. The resulting mixture was added to a solution of 100 g of p-methoxyphenol in 150 g of methylcyclohexane and this reaction mixture was hydrogenated in a stirred reactor at from 150 to 180° C. and from 3 to 8 bar of hydrogen pressure until no more hydrogen was absorbed. After a hydrogenation time of 72 minutes, 96.2% by weight of the p-methoxyphenol had reacted and p-methoxycyclohexanone had been formed in a yield of 83% by weight.

Example 2 (For Comparison)

The procedure of Example I was repeated, but the p-methoxyphenol was used in molten form without addition of methylcyclohexane. After a hydrogenation time of 380 minutes, 62.1% by weight of the p-methoxyphenol had reacted and p-methoxycyclohexanone had been formed in a yield of 46.5% by weight.

Examples 3 Bis 5

The procedure of Example 1 was repeated, but other phenols were used in a corresponding amount. Details and results are shown in Table 1.

TABLE 1

| Example No. | Phenol used | Hydrogenation time (min) | Cyclohexanone obtained (content in the reaction mixture) |
|---|---|---|---|
| 3 | p-tert-Butylphenol | 53 | p-tert-Butylcyclohexanone (91.7%) |
| 4 | Hydroquinone | 165 | p-Hydroxycyclohexanone (88.0%) |
| 5 | N-Acetyl-p-phenol | 70 | N-Acetyl-p-cyclohexanone (75.0%) |

I claim:

1. A process for preparing a cyclohexanone of the formula (I):

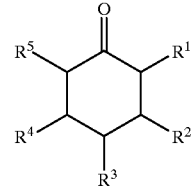

wherein $R^1$, $R^2$, $R^3$, $R^4$ and $R^5$ are each, independently of one another, hydrogen, hydroxyl, $C_1$–$C_{10}$-alkyl, $C_3$–$C_6$-cycloalkyl, $C_6$–$C_{10}$-aryl, $C_6$–$C_{10}$-aryl—$CH_2$—, $C_6$–$C_{10}$-aryl—O—, $C_1$–$C_{10}$-alkoxy, $C_3$–$C_8$-cycloalkoxy, $C_1$–$C_4$-alkylamino, di- $C_1$–$C_4$-alkylamino, $C_1$–$C_4$-acylamino, $COOR^6$ where $R^6$ is hydrogen or $C_1$–$C_4$-alkyl or $R^7$—$CH_2$— where $R^7$ is hydroxyl, $C_1$–$C_4$-alkoxy, $C_1$–$C_4$-alkylamino or di-$C_1$–$C_4$-alkylamino;

comprising:
prior to hydrogenating, forming a catalyst mixture of palladium-on-carbon catalyst, a base component, and from 20 to 200 % by weight of water, based on the base component to form a catalyst mixture, and hydrogenating a phenol of the formula (II);

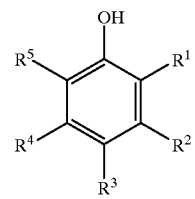

wherein $R^1$, $R^2$, $R^3$, $R^4$ and $R^5$ are defined above, in the presence of the catalyst mixture at from 100 to 250° C. and from 1 to 20 bar of hydrogen pressure and in the presence of straight-chain, branched or cyclic alkanes having a boiling point at atmospheric pressure of over 70° C. as solvents.

2. The process as claimed in claim 1, wherein, in the formulae (I) and (II), $R^1$, $R^2$, $R^3$, $R^4$ and $R^5$ represent, independently of one another, hydrogen, hydroxy, $C_1$–$C_6$-alkyl, $C_1$–$C_6$-alkoxy or $C_1$–$C_4$-acylamino and from 1 to 4 of the radicals $R^1$ to $R^5$ are different from hydrogen.

3. The process as claimed in claim 1, wherein, in the formulae (I) and (II), $R^1$, $R^2$, $R^4$ and $R^5$ represent hydrogen and $R^3$ represents hydroxy, $C_1$–$C_6$-alkyl, $C_1$–$C_6$-alkoxy or $C_1$–$C_4$-acylamino.

4. The process as claimed in claim 1, wherein the palladium-on carbon catalyst contains from 1 to 15% by weight of palladium.

5. The process as claimed in claim 1, wherein, based on the phenol of the formula (II), from 0.001 to 1% by weight of catalyst is used.

6. The process as claimed in claim 1, wherein solvents used are straight-chain or branched $C_7$–$C_{18}$-alkanes, unsubstituted $C_6$–$C_{10}$-cycloalkanes and $C_6$–$C_{10}$-cycloalkanes substituted by straight-chain or branched $C_1$–$C_{10}$-alkyl groups.

7. The process as claimed in claim 1, wherein the solvent used is isooctane, cyclohexane or methylcyclohexane.

8. The process as claimed in claim 1, wherein from 10 to 1000 ml of a straight-chain, branched or cyclic alkane having a boiling point at atmospheric pressure of over 70° C. is used as solvent per 100 g of the phenol of the formula (II) which is used.

9. The process as claimed in claim 1, wherein borax, sodium acetate or disodium hydrogen phosphate is used as base component in an amount of from 5 to 50% by weight, based on the palladium-on-carbon catalyst, and from 50 to 150% by weight of water, based on the base component, is used.

10. The process as claimed in claim 1, wherein in the formulae (I) and (II), $R_1$, $R^2$, $R^3$, $R^4$ and $R^5$ represent, independently of one another, hydrogen, hydroxy, $C_1$–$C_6$-alkyl, $C_1$–$C_6$-alkoxy or $C_1$–$C_4$-acylamino.

11. The process as claimed in claim 1, wherein the palladium-on-carbon catalyst contains from 2 to 12% by weight of palladium.

12. The process as claimed in claim 1, wherein, based on the phenol of the formula (II), from 0.05 to 0.20% by weight of catalyst is used.

13. The process as claimed in claim 1, wherein, hydrogenation of phenols of the formula (II) occurs at a reaction temperature from 150 to 200° C.

14. The process as claimed in claim 1, wherein, hydrogenation of phenols of the formula (II) occurs at a hydrogen pressure from 3 to 8 bar.

15. The process as claimed in claim 1, wherein from 50 to 300 ml of a straight-chain, branched or cyclic alkane having a boiling point at atmospheric pressure of over 70° C. is used as solvent per 100 g of the phenol of the formula (II) which is used.

16. The process as claimed in claim 1, wherein the base component used is an alkali metal salt.

17. The process as claimed in claim 1, wherein hydrogenation occurs in a stirred or loop reactor.

18. The process as claimed in claim 1, wherein the base component is first mixed with water to form a base component/water mixture, and the base component/water mixture, is then mixed with the palladium-on-carbon catalyst.

\* \* \* \* \*